US00PP26978P2

(12) United States Plant Patent
Renault

(10) Patent No.: US PP26,978 P2
(45) Date of Patent: Jul. 26, 2016

(54) ***HYDRANGEA* PLANT NAMED 'REN101'**

(50) Latin Name: *Hydrangea paniculata*
Varietal Denomination: REN101

(71) Applicant: Jean Renault, Gorron (FR)

(72) Inventor: Jean Renault, Gorron (FR)

( * ) Notice: Subject to any disclaimer, the term of this patent is extended or adjusted under 35 U.S.C. 154(b) by 63 days.

(21) Appl. No.: 14/121,327

(22) Filed: Aug. 20, 2014

Related U.S. Application Data

(60) Provisional application No. 61/959,961, filed on Sep. 5, 2013.

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS http://www.sapho.fr/gb/trees-and-shrubs/154-hydrangea-paniculata-diamantino-ren101.html; 2013; 6 pages.*

* cited by examiner

*Primary Examiner* — Kent L Bell
(74) *Attorney, Agent, or Firm* — Penny J. Aguirre

(57) ABSTRACT

A new cultivar of *Hydrangea paniculata*, 'REN101', that is characterized by its exhibits full panicles of white flowers that turn soft pink at the end of bloom, its compact and well-branched plant habit, and its early blooming habit.

2 Drawing Sheets

Genus/species: *Hydrangea paniculata.*
Varietal denomination: 'REN101'.

BACKGROUND OF THE INVENTION

The present invention relates to a new and distinct cultivar of *Hydrangea paniculata* and will be referred to hereafter by its cultivar name, 'REN101'. 'REN101' represents a new deciduous shrub grown for landscape use.

The new *Hydrangea* resulted from a controlled breeding program conducted by the Inventor in Gorron, France. The Inventor made crosses in 1998 between unnamed proprietary plants of *Hydrangea paniculata* in the Inventor's breeding program as both the female parent and male parent. The exact characteristics of the parents are unknown as seeds were pooled and sown from several crosses. 'REN101' was selected as a single unique plant in 2007 from the resulting seedlings of the above crosses.

Asexual propagation of the new cultivar was first accomplished by softwood cuttings in 2007 by the Inventor in Mayenne, France. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish in 'REN101' as a unique cultivar of *Hydrangea paniculata.*

1. 'REN101' exhibits full panicles of white flowers that turn soft pink at the end of bloom.
2. 'REN101' exhibits a compact and well-branched plant habit.
3. 'REN101' exhibits an early blooming habit.

'REN101' can be compared to the cultivars 'Limelight' (U.S. Plant Pat. No. 12,874) and 'Silver Dollar' (not patented). 'Limelight' is similar to 'REN101' in having panicles of white flowers when fully open. 'Limelight' differs from 'REN101' in having a later bloom season, in having larger panicles that are more creamy white when opening, and in having a larger plant size. 'Silver Dollar' is similar to 'REN101' in having panicles of white flowers that are similar in size. 'Silver Dollar' differs from 'REN101' in having a later bloom season and in having panicles that are pure white and do not turn soft pink at the end of bloom.

BRIEF DESCRIPTION OF THE DRAWINGS

The drawings presented are digital photographs taken of plants 5 years in age as grown in a garden in Gorron, France.

Figure 1:
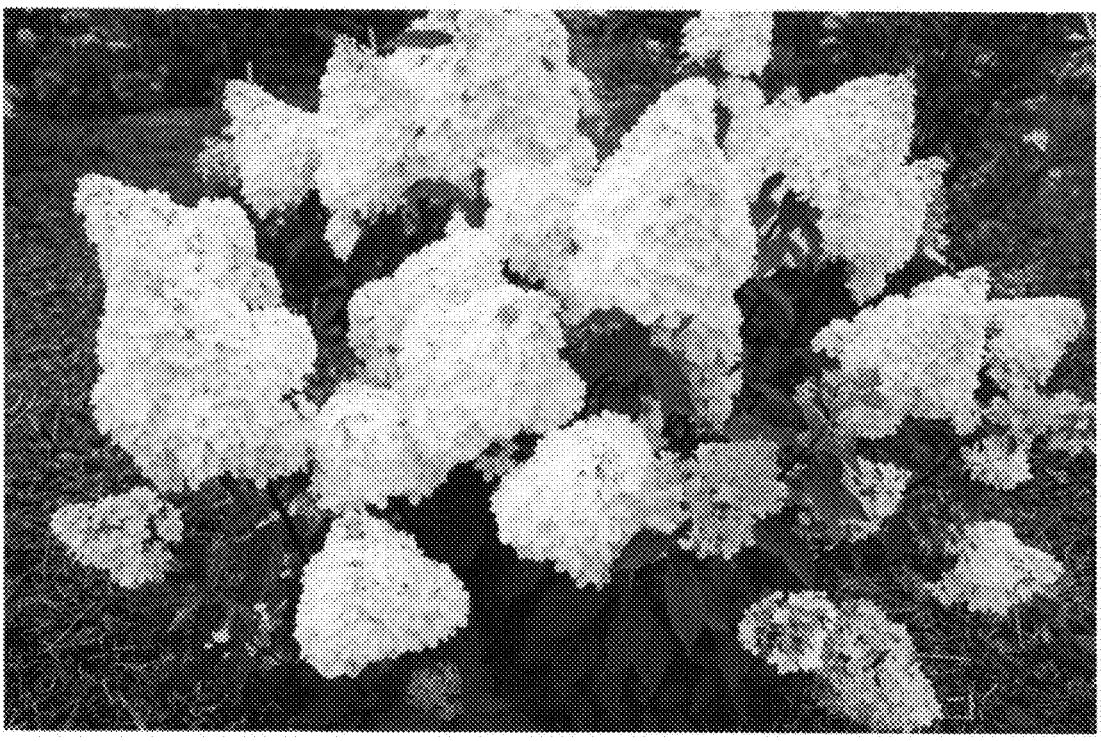
FIG. 1 provides a view of the plant habit and flowering habit of 'REN101'.
Figure 2:
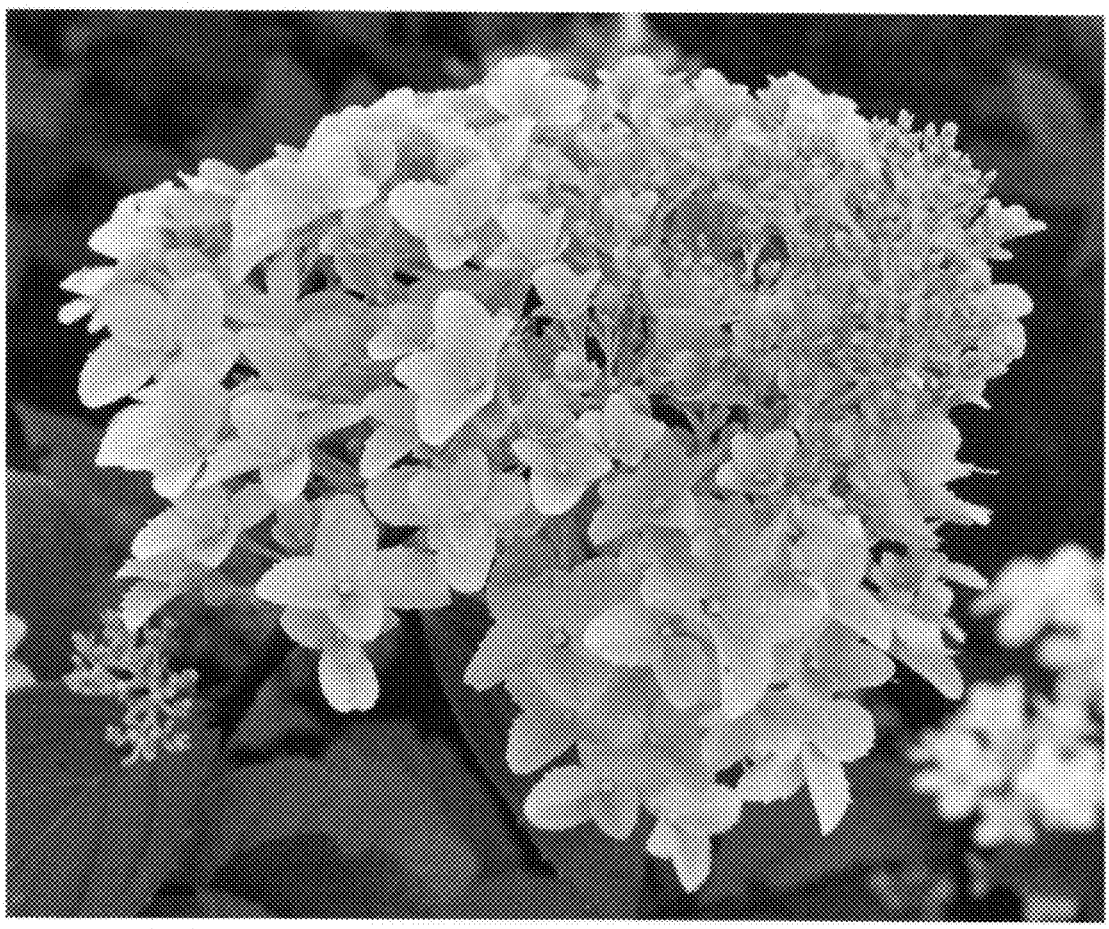
FIG. 2 provides a close-up view of a newly opened inflorescence of 'REN101'.

The colors in the photographs are as close as possible with the photographic and printing technology utilized and color values cited in the detailed botanical description accurately describe the colors of the new *Hydrangea.*

BOTANICAL DESCRIPTION OF THE PLANT

The following is a detailed description of the new cultivar as observed on 5 year-old plants of the new cultivar as grown outdoors in a trial garden in Gorron, France. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—From late July to late September in western France.

*Plant habit.*—Compact and well-branched.

*Height and spread.*—Reaches 1.2 m in height and width.

*Cold hardiness.*—At least in U.S.D.A. Zone 4.

*Diseases and pests.*—No susceptibility or resistance to diseases or pests has been observed.

*Root description.*—Fibrous.

*Propagation.*—Softwood stem cuttings.

*Growth rate.*—Moderately vigorous.

Stem description:

*Shape shape.*—Round, solid.

*Stem color.*—New wood a blend of 183A and 194A, mature wood a blend of 197A and 197C and 165A.

*Stem diameter.*—Average of 1 cm.

*Stem surface.*—Pubescent when young becoming glabrous.

*Internode length.*—Average of 10 cm.

*Branching.*—A main stem will produce an average of 4 primary branches. Subsequent branching is determined by pinching; 2 stems develop per pinched node.

Foliage description:

*Leaf shape.*—Elliptic.

*Leaf division*—Simple.

*Leaf base.*—Cuneate.

*Leaf apex.*—Primarily acuminate.

*Leaf venation.*—Pinnate, recessed, upper and lower surfaces match the surfaces of the leaf.

*Leaf margins.*—Serrated.

*Leaf attachment.*—Petiolate.

*Leaf arrangement.*—Opposite.

*Leaf surface.*—Matte on upper and lower surface, both surfaces sparsely covered with short translucent hairs, average of 1 mm in length.

*Leaf color.*—Newly formed leaves upper and lower surface; 144A, mature leaves upper surface; 137B, margins 144A, mature leaves lower surface; 147B.

*Petioles.*—Up to 1.5 cm in length and 2 mm in width, stipules absent, color is a blend of 144D and 183A.

Flower description:

*Inflorescence type.*—Full panicles.

*Lastingness of inflorescence.*—Persistent but color is retained for 4 to 6 weeks before browning.

*Inflorescence size.*—Average of 15 cm in diameter and 20 cm in length, typically observed shape is pyramidal.

*Inflorescence number.*—One per stem, new shoots develop throughout the summer.

*Flower number.*—An average of 200 sterile flowers per inflorescence and an average 80 fertile flowers per inflorescence.

*Flower fragrance.*—Faint pleasant fragrance.

*Flower aspect.*—Upright to drooping.

*Flower size.*—Sterile flowers; an average of 2 cm in diameter and 7 mm in depth, with smaller sterile flowers emerging from center an average of 1.2 cm in diameter and 5 mm in depth, fertile flowers; an average of 5 mm in diameter and 4 mm in depth.

*Flower buds.*—Sterile flowers; an average of 2 mm in length and 3 mm in width, globose in shape, 149C in color, glabrous surface, fertile flowers; average of 2 mm in length and 3 mm in width, globose in shape, NN155A in color, glabrous surface.

*Peduncles.*—Medium strength, extension of stem, average of 2 cm in length and 2 mm in width, 154D in color, surface is densely covered with very short stiff pubescent hairs matching peduncle color, average hair size is 0.5 mm in length, held between angles of 40° and 50°.

*Pedicels.*—Sterile flowers; moderate strength, an average of 1 cm in length and 1 mm in width, 154D in color, surface is moderately covered with very short soft pubescence matching pedicel color, average hair size is 0.5 mm in length, held between angles of 40° and 60°, fertile flowers; moderate in strength, an average of 2 mm in length and 1 mm in width, 145C in color, surface is smooth and dull, held between angles of 40° and 60°.

*Sepals.*—Sterile flowers; 3 to 4, un-fused, not overlapping, rotate in arrangement, smooth, dull and glabrous on both surfaces, broadly elliptic to broadly ovate in shape, held slightly upwards when fully open, entire margin, apex is rounded to broadly acute, average of 1 cm in length and 9 mm in width with smaller flowers emerging from center that are an average of 7 mm in length and 5 mm in width, color upper and lower surface when newly opened in mid-summer, 144B, color when maturing in mid summer upper and lower surface; 154D, fertile flowers; 5 fused in campanulate calyx, average of 1 mm in length and width, 145D in color, glabrous on both surfaces.

*Petals.*—Sterile flowers (petal eye); 3 mm in diameter, 1 mm in depth, 154D in color, fertile flowers; 155C in color when mature in mid summer, an average of 3 mm in length and 2 mm in width, rotate in arrangement.

Reproductive organs (fertile flowers):

*Stamens.*—Average of 9, anther is about 1 mm in length and a blend of 199B and 203B in color, filament is an average of 4 mm in length and 158B in color, pollen is minute in quantity and 162A in color.

*Pistils.*—Average of 3, average of 2 mm in length, 157A in color, style is an average of 1 mm in length and 155A in color, stigma is club shaped and 158B in color (newly opened blooms).

*Fruit and seed.*—None observed.

It is claimed:

1. A new and distinct cultivar of *Hydrangea* plant named 'REN101' as herein illustrated and described.

* * * * *